United States Patent [19]

Place

[11] Patent Number: 4,962,047

[45] Date of Patent: Oct. 9, 1990

[54] MIXING AND SEPARATING SOLID PHASE SUPPORTS BY PRESSURE VARIATION

[75] Inventor: John F. Place, Geneva, Switzerland

[73] Assignee: IntraCel Corporation, Bridgetown, Barbados

[21] Appl. No.: 924,033

[22] Filed: Oct. 28, 1986

[30] Foreign Application Priority Data

Oct. 30, 1985 [CH] Switzerland ............................ 4694/85

[51] Int. Cl.$^5$ ................ G01N 33/543; G01N 33/537; G01N 33/544; C12N 11/00
[52] U.S. Cl. .................................... 436/518; 435/174; 435/177; 435/178; 435/180; 435/803; 435/814; 436/528; 436/531; 436/534; 436/536; 436/538; 436/824; 530/810
[58] Field of Search ............... 435/174, 177, 188, 180, 435/182, 803, 814; 436/518, 528, 529, 531, 534, 824, 536, 538; 530/810, 815

[56] References Cited

U.S. PATENT DOCUMENTS

| | | | |
|---|---|---|---|
| 2,525,232 | 10/1950 | McCaughy | 272/8 N |
| 3,421,893 | 1/1969 | Taylor | 430/215 |
| 3,957,580 | 5/1976 | Nelson | 435/180 |
| 4,070,348 | 1/1978 | Kraemer et al. | 435/180 X |
| 4,222,238 | 9/1980 | McCulloch | 60/398 |
| 4,237,229 | 12/1980 | Hartdegan et al. | 435/180 X |
| 4,352,883 | 10/1982 | Lim | 435/188 |
| 4,448,409 | 5/1984 | Kaga et al. | 272/8 N |
| 4,530,900 | 7/1987 | Marshall | 436/824 X |
| 4,576,718 | 3/1986 | Reischl et al. | 435/182 X |
| 4,656,143 | 4/1987 | Baker et al. | 436/824 X |

OTHER PUBLICATIONS

Trevan, M. D., Immobilized Enzymes, John Wiley & Sons, N.Y. 1980, pp. 66–70.
Braun et al., "Cellular and Foamed Plastics as Separation Media", TALANTA, vol. 22, pp. 699–705, Pergamon Press, 1975, Great Britain.

*Primary Examiner*—David M. Naff
*Attorney, Agent, or Firm*—Cushman, Darby & Cushman

[57] ABSTRACT

Gas containing granules of a resiliently compressible material having a density variable with pressure are used as a solid phase support in liquid phase reactions such in immunological reactions. Varying pressure causes the density of the granules to change and is used for mixing and separating the granules in liquid phase. In an immunological reaction, the granules having an attached antibody are combined with a solution containing an antigen, then varying pressure is applied to the solution to mix the granules in the solution to fix the antigen to the antibody and then pressure on the solution is varied to force the granules to the top or bottom of the solution whereby the solution can be separated from the granules.

3 Claims, 1 Drawing Sheet

MIXING AND SEPARATING SOLID PHASE SUPPORTS BY PRESSURE VARIATION

BACKGROUND OF THE INVENTION

The invention relates to a solid-phase support for a component adapted to participate in a reaction in a liquid phase Solid-phase granules are finding increasing applications in liquid-phase reactions, for the purpose of analysis (e.g. solid-phase immunological tests) and also in manufacturing processes (e.g. immobilised enzyme or cell systems for industrial fermentation).

In most immunological tests, a tracer is used for measuring the distribution of antigen-antibody complexes and antigens or antibodies alone in the reversible-bond antigen-antibody reaction, when the distribution between the bonded complexes and the free parts is proportional to the initial concentration of antigens-antibodies before the reaction Provided the immunological test tracer is not modified by the bonding reaction (as in homogeneous tests, e.g. EMIT ® Syva, U.S.A.), the determination process is facilitated by separating the bonded complexes from the free parts of the test (as in a heterogeneous test). This result is often obtained by fixing a test component to a solid phase which is physically separated from the liquid phase after the incubation reaction A number of variants of heterogeneous tests is known and described in the literature.

A number of different types of solid phases intended for heterogeneous bond tests is commercially available. The available range extends from single-support systems such as coated balls or tubes, to microcrystalline cellulose or fine-particle silica. The choice of solid phase for a given test will depend on a number of factors, inter alia the ability to be associated with a bonding agent (relative to the total available surface area) and the convenience of use.

The disadvantage of these solid phases are that they have to be dispersed in the liquid phase in order to bring about a complete reaction (at equilibrium) with the reagent or reagents in solution, and they must then be separated from the aqueous phase before measuring the result of the reaction.

A solid-phase support for immunological tests therefore has to satisfy two contradictory requirements. To obtain optimum dispersion of the solid phase resulting in an efficient reaction and consequently a sensitive test, it is necessary for the solid phase to have the largest possible surface area in a given volume, and this can be obtained with fine granules. On the other hand, separation of the solid phase will be better in proportion as the granules are larger. The adopted methods usually try to make a compromise between these two contradictory requirements and discover the most efficient methods of mixing and separation.

For the purpose of mixing, for example, it has been proposed to vibrate the reaction tubes around a transverse axis at the centers of the respective tubes, or intermittent vortex mixing, or intermittent agitation or use of fine granules. For the purpose of separation, use has been made of centrifuging and repeated washing of the solid phase (with intermediate mixing), or of a saccharose gradient, or ferromagnetic particles, plastics balls, etc.

Ferro-magnetic particles can easily be separated from the liquid by using a magnetic field. Although these particles are relatively heavy, they remain fairly well in suspended in the liquid phase, provided they are very finely divided. These particles, however, are difficult to re-suspend in the liquid phase.

Irrespective of the nature of the solid-phase supports in the form of particles or the aforementioned granules for suspending in the liquid phase, it is necessary to use two different techniques for measuring and separating the particles or granules. Frequently, these techniques are difficult to operate in an automatic analysis installation. The mixing operation, for example, which should be performed without risk of contamination and without removing the product, should preferably avoid any contact with the liquid for analysis. Agitation techniques, particularly with very small volumes of liquid, are not always efficient or reproducible, owing to the surface tension inter alia, against the vessel walls. Separation by centrifuging usually necessitates transferring the analysis tube to a centrifuging rotor, which increases the complexity of the installation and the process of analysis and also increases the cost and the amount of manipulation.

An intermediately-sized solid phase is a compromise between the two extremes, i.e. finely divided particles and a single support. An aforementioned intermediate-size solid phase has an adequate bonding-agent capacity and, if its density is substantially equal to that of the liquid phase, it can remain in suspension during the incubation phase of the main reaction.

Patent Application EP-A-O 123 403 relates to intermediate-sized particles which are slowly separated by gravity. The disadvantage of separation during incubation is avoided by substantially increasing the density of the liquid phase during incubation (e.g. by adding saccharose). However, this method has certain disadvantages. For example, addition of an agent for modifying the density mat influence the reaction as a result of chemical or physical effects on the bonding properties. Addition and dilution of the aforementioned agent in the liquid phase may affect the balance obtained and necessitate additional steps in the test.

Solid phases are also being increasingly used in sectors other than immunological analysis, e.g. in biological and biochemical reactors. Some cells and micro-organisms can be more efficiently cultivated on suitable surfaces such as 50–300 μm microsupports, e.g. Cytodex ® produced by Pharmacia (Sweden) and used for production of viruses, interferon and antibodies. Viruses and vaccines are produced in this manner in 100–1 000 litre reactors using solid-phase support particles.

Since micro-organisms grow and can undergo a number of undesirable secondary reactions, it is sometimes preferable to mass only those enzyme systems necessary for the desired mass reaction. These enzymes are soluble in the liquid phase and will therefore be washed in a continuous reactor. For this reason they are often immobilised on solid phases. Although the whole organisms or cells are more stable and they can synthesise their own enzymes and arrange the steric positioning of the reagents in the required reactions, enzymes are often used for practical reasons, i.e. for monitoring and for obtaining a pure product.

Cultivation of mammal cells is often the only appropriate means of producing mammal proteins, since mammal cells undergo a number of the post-translational modifications necessary for producing functional molecules. Co-ordination of mammal cells is difficult owing to the fragility of the cells, which are sensitive to conventional mixing methods such as mashing and stirring Since mammal cells grow relatively slowly, it is important to maintain aseptic conditions and avoid an accumulation of microbial products which may reduce the growth of cells.

Mammal cells are grown by two methods — in free homogeneous suspension (under good cultivation conditions) and in immobilised form with perfusion by the liquid phase (e.g. in hollow-fibre reactors, fluidised beds or on spongy or ceramic matrices.)

Conventional mixing devices comprise mechanisms for moving, agitating or rotating the reaction vessel or conveying air bubbles through the reaction medium These mixing processes have disadvantages. Mashing of the liquid results in dislocation through shearing and the seal of the mashing shaft is a source for contaminating the reactor. Agitation and rotation of the reactor are not very efficient and cause contamination of the reactor walls. Mashing with air bubbles may result in the formation of foam and contamination of the reactor walls.

Perfusion reactors are being increasingly used for large-scale production of substances having a high added value, such as monoclonal antibodies. The disadvantage of hollow-fibre reactors is the pressure drop associated with perfusion through hollow fibres and the possibility of forcing pockets of isolated cells in a microenvironment. Consequently, some manufacturers still prefer to use suspension reactors in the form of a fluidised bed.

As in immunological tests, the main problems of using solid phases relate to the mixing of the solid phases with the reagents, to ensure a complete reaction and subsequent separation of the reaction products in the liquid phase. In large-scale production, mixing is also important in transferring the heat of reaction and distributing the gas in the liquid phase.

SUMMARY OF THE INVENTION

The obJect of the invention is at least partly to obviate the aforementioned disadvantages associated with the nature of the solid-phase supports proposed hitherto.

To this end, the invention relates to a solid-phase support for a component for participating in a reaction in a liquid phase.

One main advantage of the support is that a single means (i.e. mainly variations in pressure) can be used to mix and also to separate the solid-phase support from the liquid phase. Mixing is brought about without contact with the liquid and without subjecting the liquid-holding vessel to repeated acceleration and deceleration. Alternating variations in pressure can be used to move the solid-phase supports all the way up and down the liquid phase, irrespective of the viscosity of the liquid or the surface tension of the liquid against the vessel walls. Solid-phase supports can be separated from the liquid phase by bringing about a pressure, which gives the supports a density either higher or lower than that of the liquid. As can be seen, these supports are of use in all the aforementioned applications, both in methods of analysis and in chemical or biological reactors, the advantages in each case being efficiency of mixing and separating the solid phase and the simplicity of the methods used.

The variable-density supports according to the invention are obtained by including gases in the form of one or more cells in a solid phase or a resiliently deformable material using the technique of expanded plastics, which differ from spongy structures in that their cells have closed pores. This technique for producing expanded plastics is described e.g. in an article by G. R. Thomas in "Biotech Plastics" September 1965 (pages 552–558) under the title "The Formation of Cellular Plastics" The example described hereinafter therefore is non-limitative and use can be made of all known techniques for including gases by chemical methods using swelling agents, or by physical methods by evaporation or expansion at low pressure or by mechanical methods by including gases or hollow micro-spheres. Reference may therefore be made to the abundant literature on this subject with regard to the construction of solid-phase supports having a variable density with pressure.

BRIEF DESCRIPTION OF THE DRAWINGS

The accompanying drawings diagrammatically illustrate, by way of example, the procedure in immunological tests using two variants of the solid-phase support according to the invention.

DETAILED DESCRIPTION

Figure 1F:
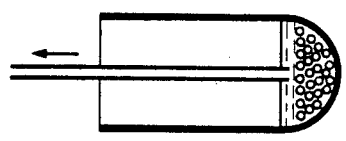
FIGS. 1a–1f relate to the various steps in an immunological test using the first variant of the support, and FIGS. 2a to 2f relate to the various steps of the same immunological test using the second variant of the support.
Figure 2F:
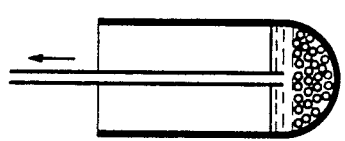

A more detailed description of an aforementioned support associated with an antibody for forming a solid-phase support constituting the solid phase in an immunological test is provided hereinbelow.

In this example, a 4% solution of alginate (Protanal ® LF 20/60 produced by Protan A/S, Drammen, Norway) was formed in distilled water heated to 80° C. for 10 minutes, the resulting viscous liquid being cooled to ambient temperature.

A very small quantity of detergent (0.01% of Tween ® LF 20/60 by Merck-Schuchardt, Munich) was then incorporated in the solution by foaming it with a propeller driven at 4 000 rpm, and the solution was distributed dropwise through a pipette having its tip 40 cm above the level of a solution of 0.1 $CaCl_2$, which was constantly agitated by a magnetic bar rotating at 250 rpm.

The resulting granules were about 1 mm in diameter and enclosed gas cells. They were then washed in a number of baths of a solution of 0.1 M $CaCl_2$.

A solid-phase antibody for an enzymatic tracer immunological test for testing human immuno gamma globulin (IgG) is prepared as follows: 25 ml of granules prepared as in the aforementioned example are taken in suspension in the solution of 0.1 M $CaCl_2$ and progressively transferred to acetone in successive steps by intermediate washing in acetone-water where the concentration of acetone is 10 : 90, 50 : 50, 80 : 100 and 100 : 0 in the successive steps.

The 25 ml of granules are then suspended in acetone, the total volume being 50 ml. 3 g of carbonyl-diimidazole (Sigma Chem. Co) are then added, the substance being a bridging agent for the protein (antibody) to be fixed to the granule. The mixture is then agitated for 3 hours at 20° C. by vibration through an amplitude of 180° around a central transverse shaft. The excess bridging agent is then removed by repeated washing of the granules with acetone. The thus-activated granules are then balanced with an aqueous test buffer comprising 0.05 mol/l of Barbitone ®, which is a diethyl barbituric acid produced by Fluka, Buchs (Switzerland) adjusted to pH 8.0 with sodium hydroxide (Merk, Darmstadt) and containing 0.005 M $CaCl_2$. The concentration of the buffer solution relative to acetone is increased stepwise as follows: 10 : 90, 20 : 80 and 100 : 0.

After the balancing operation, an antibody is immediately bridged to the activated granules. A solution of proteins (antibody) is added to the 25 ml of granules, the quantity of solution being sufficient to obtain a final volume, with the Barbitone buffer, of 50 ml. The protein used was an enriched fraction of anti-human sheep immuno gamma globulin (Scottish Antibody Production, Carluke, Scotland) which reacts with the granules at a final concentration of 5 mg of protein/ml of total volume. After agitation by vibrating the test substance through an amplitude of 180° around a central transverse shaft for 16 hours, the granules are separated from the liquid phase. In order to remove substances adhering in non-covalent mannner to the granules, the granules are then repeatedly washed alternately at pH 2.0 and pH 8.0. The measured concentration of proteins bonded to the granules was about 1 $\mu g/cm^2$.

The granules prepared by the aforementioned process and bonded to the antibodies are about 1 mm in size. They are then prepared for use for an immunological test on a sample of human serum to be analysed. The test procedure will be described hereinafter.

In a first step, a check was made of the sensitivity of the solid-phase granules bridged to the antibodies and obtained by the process previously described. To this end, on each occasion, two tests were analysed, using two samples of granules obtained with solutions of antigens consisting of normalized IgG (with concentrations from 0.1 to 100 $\mu g/ml$) prepared in the test buffer (Barbitone ® 0.05 mol/l, pH 8.0) with 2% v/v of normal sheep serum adapted to fill the sites not occupied by the antigens. The analyses were made by adding 100 $\mu l$ of solution of normalized antigens to 103 $\mu l$ of test buffer, followed by 50 $\mu l$ of buffer and 50 $\mu l$ of anti-human antibodies tagged by an enzyme (Peroxidase by Dakopatts, Copenhagen, Denmark) diluted in a final ratio of 1 : 500 in a buffer.

After incubation at 22° C. for 90 minutes, the granules were washed three times with the test buffer and twice with the enzymes buffer (0.15 mol/l, acetate pH 5.0 buffer). The colorimetric reaction for detecting the immobilised tagged specific antibody was brought about by adding 300 $\mu l$ of chromogenic solution (20 mg/l orthophenanthraline diamine), 20 $\mu l$ of a solution of 50% $H_2O_2$, 50 ml of acetate buffer (0.1 mol/l, pH 5.0) and incubation at 22° C. for 30 minutes. The colorimetric reaction was stopped and stabilized by adding 1 ml of 0.1 N $H_2SO_4$. The absorption rate was measured at 450 nm relative to 0.1N $H_2SO_4$ alone.

The following table, in the case of both samples, shows the relation in dependence on the reading obtained with the enzymatic tagging immunological test for human IgG, using granules according to the invention.

TABLE

| Concentration of human IgG | Sample 1 at 450 nm | Sample 2 at 450 nm |
| --- | --- | --- |
| 0 | 0.105 | 0.098 |
| 0.1 | 0.101 | 0.107 |
| 0.5 | 0.220 | 0.190 |
| 1.0 | 0.311 | 0.290 |
| 5.0 | 0.589 | 0.575 |
| 10.0 | 0.701 | 0.705 |

TABLE-continued

| Concentration of human IgG | Sample 1 at 450 nm | Sample 2 at 450 nm |
| --- | --- | --- |
| 50.0 | 0.795 | 0.789 |
| 100.0 | 0.895 | 0.926 |

The resulting sensitivity is estimated at about 0.5 $\mu g$ IgG/ml.

We shall now by way of example describe two immunological test procedures using two variants of variable-density granules as solid-phase supports of anti-human IgG antibodies.

First, we refer to FIGS. 1a to 1f in the description of the first procedure. In a first step (FIG. 1a) a given volume of sample 2 for analysis or of a standardized solution used in parallel (when it is desired to make a comparative test) is introduced into test tube 1 with a given quantity of an enzymatic tracer. A given volume of buffer 3 is added together with a portion 4 of granules 5 comprising solid-phase antibody supports according to the invention.

In this example, the density of the granules is below that of the liquid, so that at atmospheric pressure and ambient temperature the granules remain at the surface of the liquid.

In the second step of the process, the contents of test-tube 1 is alternately subjected to pressures varying between atmospheric pressure and a higher pressure chosen so that the volume of granules 5 decreases sufficiently to give them a density higher than that of the liquid, so that the granules fall towards the bottom of test-tube 1 and then rise when the pressure varies. Once the granules are in suspension (FIG. 1b) an intermediate pressure can be maintained or permanently varied. During this period, which corresponds to incubation, the liquid is kept at a predetermined temperature for a given time.

Figure 1E:
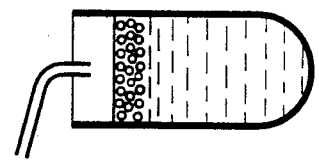
Figure 2E:
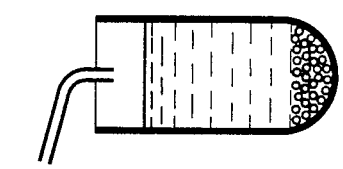

When incubation is complete, the pressure is brought to its higher value in order to move all granules 5 to the bottom of tube 1 (FIG. 1c) and the supernatant liquid is sucked through a duct 6 (FIG. 1e).

Figure 1D:
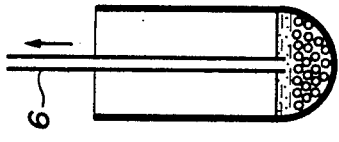
Figure 2D:
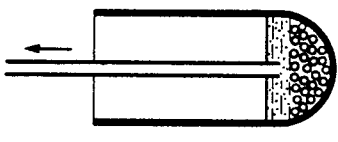
Figure 1C:
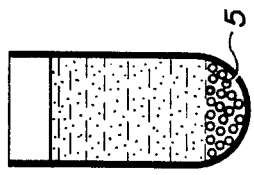
Figure 2C:
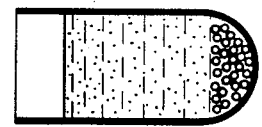
Figure 1B:
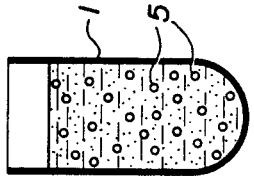

In the next operation, atmospheric pressure is restored and a washing buffer is added to granules 5, after which the operations in FIGS. 1b to 1d are repeated with the washing liquid. A number of successive washing operations are performed in this manner.

The next phase is to colour a solution comprising an enzymatic reagent as described hereinbefore, by re-mixing the granules in the solution as already done (FIG. 1b) and incubating at controlled temperature, after which the aforementioned solution is added.

To block and stabilize the reaction, the pressure is increased to its upper value (FIG. 1c) in order again to collect the granules at the bottom of tube 1. Conventional measurements can then be made., more particularly in the present case, the measurements can be of the absorption rate of electromagnetic radiation by the liquid at a given wavelength, by sucking the liquid (FIG. 1f) into a photometer (not shown) or measuring it through the tube. Alternatively a gamma count can be made of granules where the antibody has reacted with a human antigen, in the case of an isotopic tracer.

As the preceding description shows, variable-density granules used as solid-phase support of one component in a reaction, in the present case an immunological reaction, can enable the solid phase to be mixed and separated without acting on the tube itself but only by acting on its contents and only through pressure, i.e. without contact with the liquid phase. The reaction process is particularly suitable for automation, since only a source of variable pressure is necessary for performing the entire process. It is only necessary to isolate the tube from atmosphere and connect it to a source of pressure. The mixing and the separation efficiency are completely reproducible and reliable.

Figure 2B:
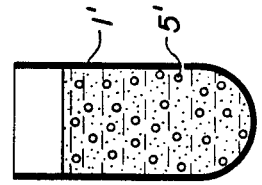
Figure 1A:
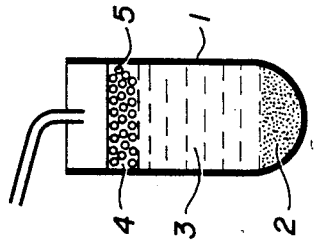
Figure 2A:
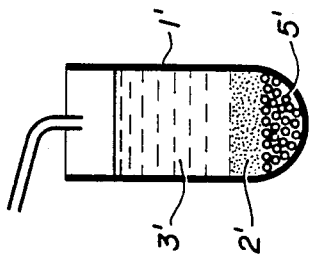

In the variant illustrated in FIGS. 2a to 2f, the only difference is that granules 5' have a density at atmospheric pressure greater than the density of the liquid, so that they are normally at the bottom of test-tube 1'. In this case, therefore, an alternating pressure variation which is negative relative to atmospheric pressure has to be applied to the liquid to raise the granules and mix them or to suspend them in the liquid phase (FIG. 2b). The granules can be separated so as to suck the liquid, simply by restoring atmospheric pressure. This may have advantages over the preceding variant, in that all operations other than mixing or suspending the granules, as illustrated in FIG. 2b, occur at atmospheric pressure, and it is easier to maintain a negative pressure in a closed chamber than to maintain pressure. In other respects the test procedure is similar to that previously described.

In another variant, the solid-phase granules have practically the same density as the solid phase at ambient temperature and pressure. In this variant, the granules remain in suspension during the incubation phase corresponding to FIGS. 1a or 2b and pressure variations are used to separate the solid phase or return it to suspension. This variant has the additional advantage that incubation can be brought about in any suitable vessel without special equipment.

As already mentioned, solid-phase granules used as support for a component in a biochemical or chemical reaction can be used in applications other than the described immunological tests. These supports are of use in other types of analysis and in manufacturing processes using tanks or continuous reactors. In the aforementioned continuous reactors, where a flow of reagents continuously enters the vessel and the products containing the aqueous phase continuously flow out of it, the solid-phase granules can be kept suspended in the reaction medium by suitably adjusting the pressure. The negative buoyancy of the granules can be adjusted against the ascending motion of the reagents, thus obtaining a sort of fluidized bed which is less dependent on the flow speed of the liquid phase.

In the case of cell cultivation, it is known that granules collected in a reduced space will increase the formation of aggregates of particles and cells, increasing the cultivation yield. In US-A-4 335 215, it has been proposed to obtain this effect by periodic transfer of a suspension of microsupports in a separate, reduced-volume drum. If the solid-phase granules according to the invention are used, it is possible to concentrate them at either the top or the bottom of a reactor to assist the formation of aggregates, without transferring the suspension from the main reactor body.

The variable-density granules may also be used as a solid-phase support for chromatographic separation of organic or inorganic compounds from a liquid (aqueous) phase, by covering the solid-phase support by a substance, e.g. an adsorbent substance, capable of separating the compound in solution from the liquid phase. If the granules are placed in a flow of the liquid phase, the pressure can be adjusted to prevent them being entrained by the flow. In the case of discontinuous separation, the granules can be moved in the liquid by varying their density as previously described.

Of course, centrifugal force may be one suitable method of varying the hydrostatic pressure applied to variable-density granules in order to reduce their volume and increase their density.

Hitherto we have described applications in which the granules according to the invention are solid-phase supports of a component adapted to participate in a reaction, or of a material capable of fixing a component in solution. There are many cases, however, where mixing of two or more components in a liquid phase poses problems which are inadequately solved by known methods. In many of these cases, the use of granules having a density variable with pressure will provide a solution even though the granules do not, as hitherto, constitute a support for a component in a reaction. In such cases, the granules will not act as mixing means. They can therefore be larger than the previously-described granules, so as to move larger volumes of liquid and thus help to form eddies in the liquid.

I claim:

1. A method of separating a component from solution comprising the steps of
   (a) combining a solid phase support coated with a material attractive to said component with a solution containing the component, the support being in the form of gas containing granules of a resiliently compressible material having a volume capable of varying with pressure;
   (b) varying pressure applied to said solution to vary the volume of said granules so as to mix said granules in said solution by changing the density of said granules and thereby attach said component to said support;
   (c) varying pressure applied to said solution to vary the volume of said granules so as to force the granules to the top or bottom of the solution by changing the density of said granules; and
   (d) separating the solution from the granules.

2. A method of separating a component in liquid phase using a solid-phase support comprising the steps of:
   (a) combining gas containing granules of a resiliently compressible material having a volume capable of varying with pressure which have associated an agent for fixing said component, with a liquid phase containing the component;
   (b) varying pressure applied to said liquid phase to vary the volume of said granules so as to mix said granules in said liquid phase by changing the density of said granules and thereby fix said component to said granules; and
   (c) subsequently varying the pressure applied to said liquid phase to vary the volume of said granules so as to separate said granules from said liquid phase by changing the density of said granules.

3. The method of claim 2 wherein said component in the liquid phase is an antigen and the agent for fixing the component is an antibody.

* * * * *